United States Patent
Suissa

(10) Patent No.: US 12,090,263 B1
(45) Date of Patent: Sep. 17, 2024

(54) LIPOSUCTION APPARATUS

(71) Applicant: Squlpt Management LLC, Agoura Hills, CA (US)

(72) Inventor: Daniel Suissa, Aventura, FL (US)

(73) Assignee: Squlpt Management LLC, Agoura Hills, CA (US)

( * ) Notice: Subject to any disclaimer, the term of this patent is extended or adjusted under 35 U.S.C. 154(b) by 0 days.

(21) Appl. No.: 17/572,052

(22) Filed: Jan. 10, 2022

(51) Int. Cl.
*A61M 1/00* (2006.01)

(52) U.S. Cl.
CPC ........... *A61M 1/89* (2021.05); *A61M 2202/08* (2013.01); *A61M 2205/10* (2013.01)

(58) Field of Classification Search
CPC ........... A61M 1/89; A61M 1/77; A61M 1/76; A61M 1/84; A61M 1/85; A61M 1/774; A61M 2202/08; A61M 2202/0014; A61M 1/0058; A61M 1/0062; A61M 1/772; A61M 1/00; A61M 3/0283; A61M 39/14; A61M 39/105; A61B 17/32002; A61B 2217/005; A61B 2217/007; A61B 2017/32007; A61B 2017/320032; A61B 2217/32007; A61B 2217/32002; Y10S 604/902; A61C 17/0208
See application file for complete search history.

(56) References Cited

U.S. PATENT DOCUMENTS

| 5,792,098 | A | * | 8/1998 | Felix | A61M 1/85 |
| | | | | | 604/27 |
| 6,013,048 | A | * | 1/2000 | Podany | A61B 8/546 |
| | | | | | 604/35 |
| 6,336,925 | B1 | | 1/2002 | Malak | |
| 6,371,934 | B1 | * | 4/2002 | Jackson | A61B 17/00234 |
| | | | | | 604/35 |

(Continued)

FOREIGN PATENT DOCUMENTS

| WO | WO-9748427 A2 | * | 12/1997 | .......... | A61M 1/0064 |
| WO | WO-2017048776 A1 | * | 3/2017 | ............. | A61B 50/20 |
| WO | WO-2021119286 A1 | * | 6/2021 | ............. | A61M 1/76 |

OTHER PUBLICATIONS

Seal Sales. O-rings. [online], [retrieved on Aug. 7, 2023]. Retrieved from the Internet <URL: https://www.sealsales.com/o-rings/O-Rings.html> (Year: 2023).*

*Primary Examiner* — Nicholas J. Weiss
*Assistant Examiner* — Linnae E. Raymond
(74) *Attorney, Agent, or Firm* — NK Patent Law

(57) ABSTRACT

This disclosure relates to an improved liposuction apparatus having a handpiece. The handpiece may have a handpiece suction pathway extending through the handpiece from a front end to a back end of the handpiece and a handpiece infiltration fluid pathway extending through the handpiece from the front end to the back end of the handpiece, the handpiece suction pathway and the handpiece infiltration fluid pathway being separate and distinct. The handpiece may be configured such that, when a suction cannula having (Continued)

a suction cannula pathway is attached to the front end of the handpiece, the suction cannula pathway and the handpiece suction pathway are in fluid communication with one another. And, when an infiltration fluid cannula having an infiltration cannula pathway is attached to the front end of the handpiece, the infiltration cannula pathway and the handpiece infiltration fluid pathway are in fluid communication with one another.

9 Claims, 15 Drawing Sheets

(56) References Cited

U.S. PATENT DOCUMENTS

2003/0105422 A1\* 6/2003 Gonon .................... A61M 1/89
 604/21
2022/0249120 A1\* 8/2022 James ............ A61B 17/320068

\* cited by examiner

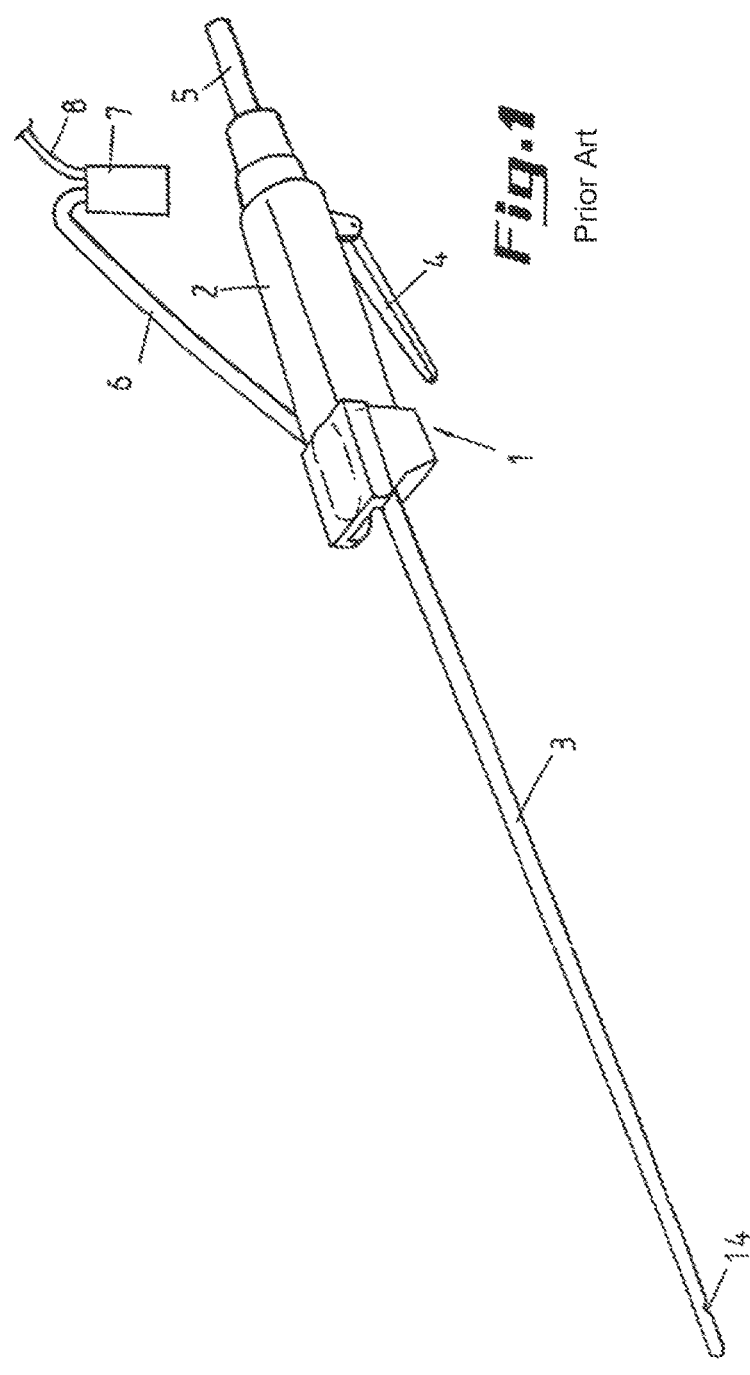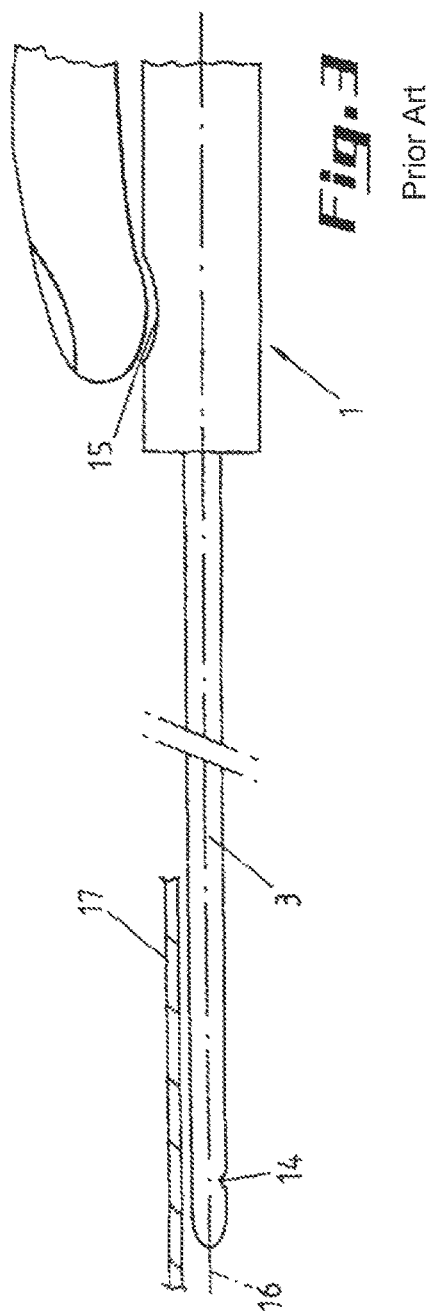
Fig. 1
Prior Art
Fig. 3
Prior Art

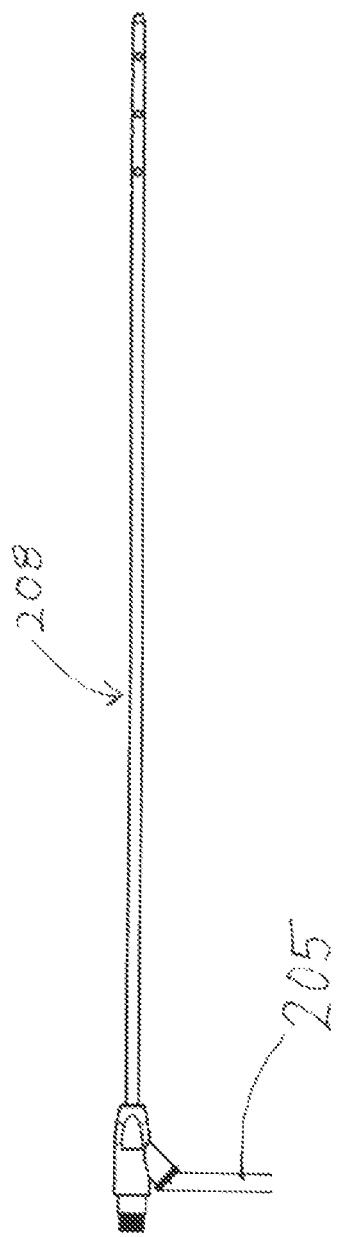

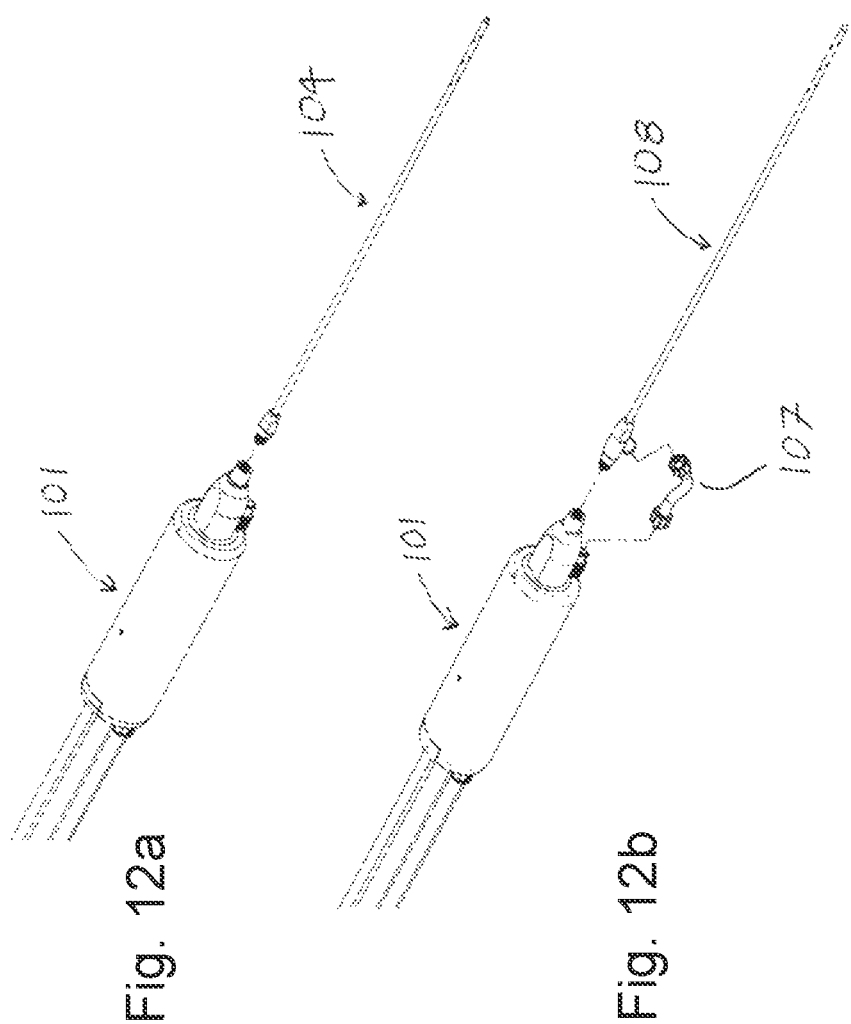

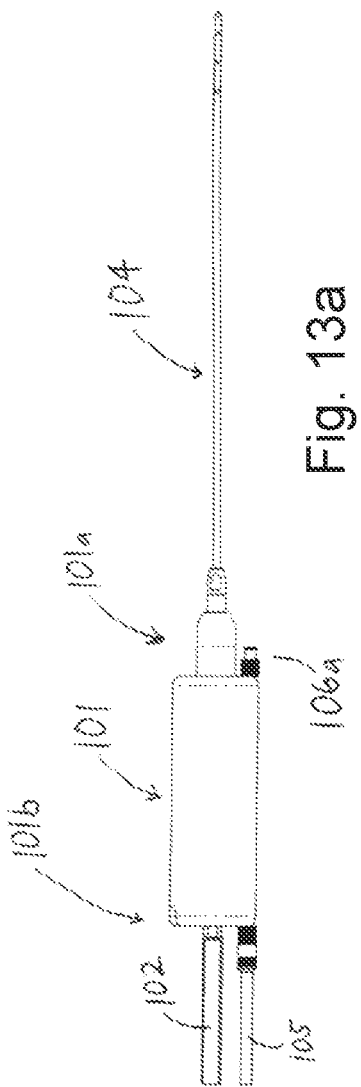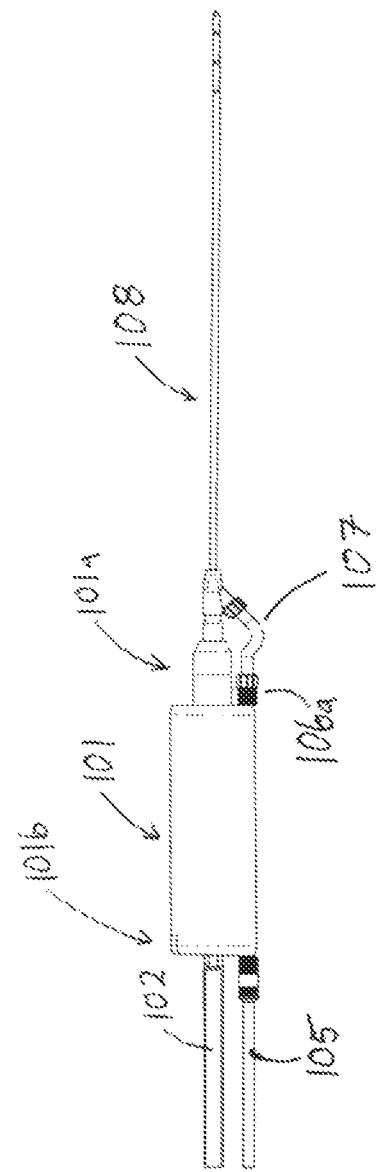

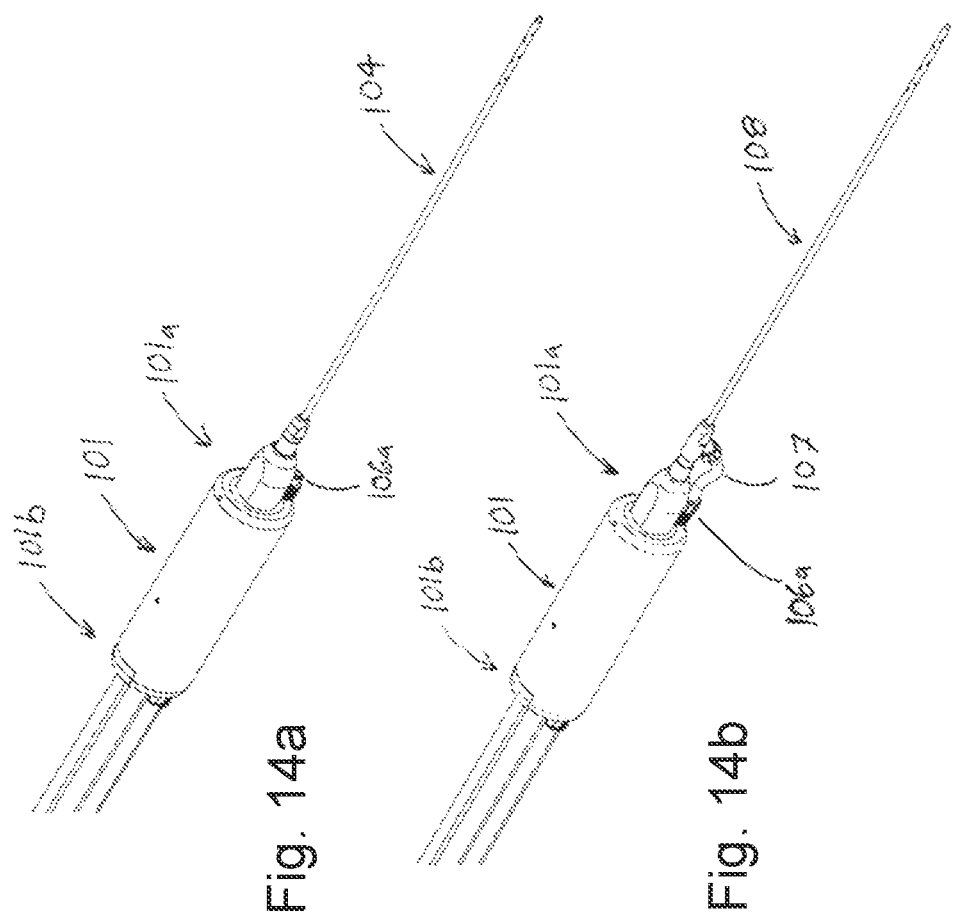

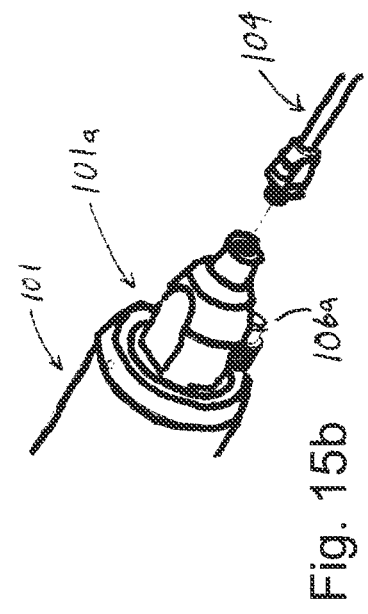
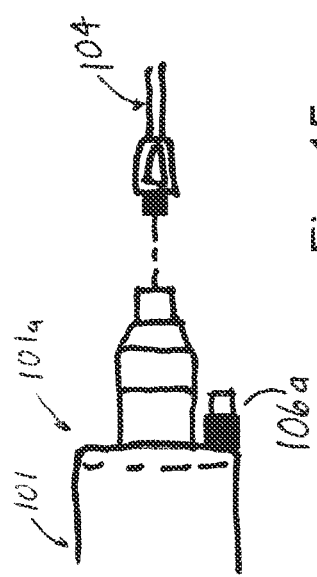
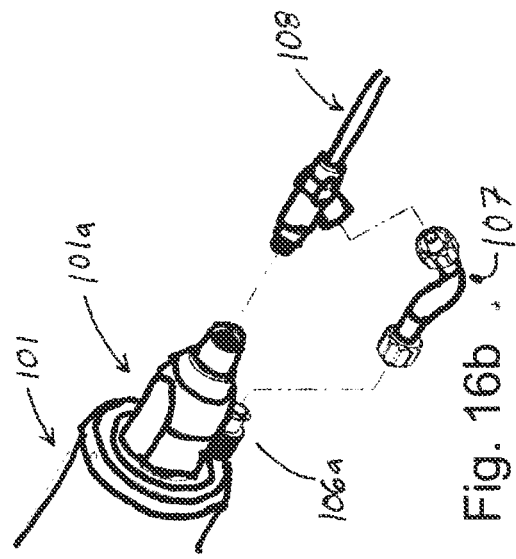
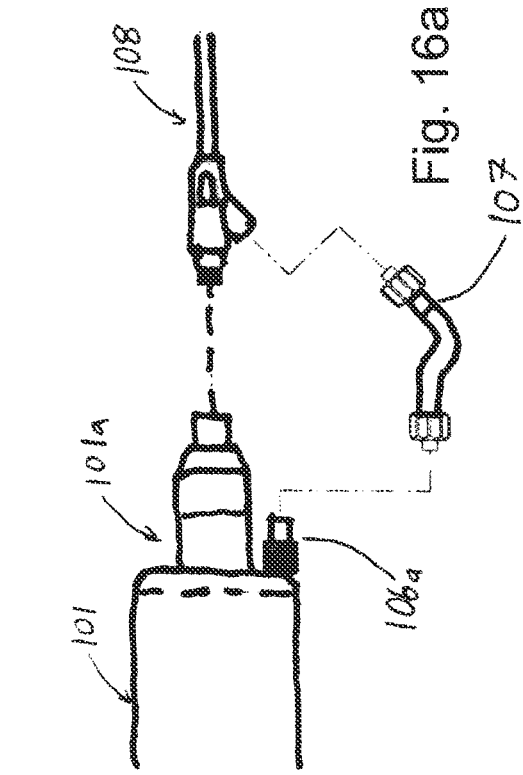

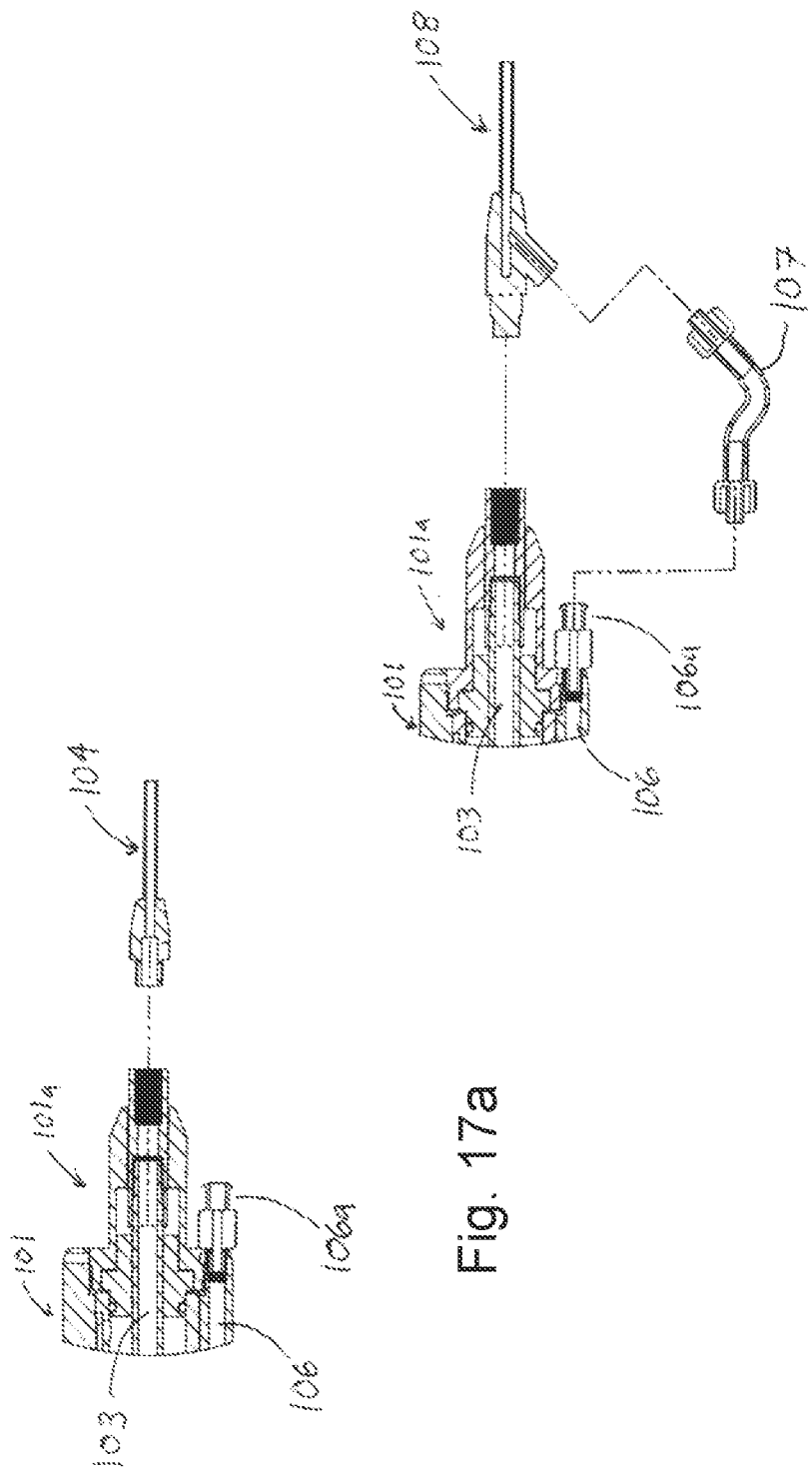

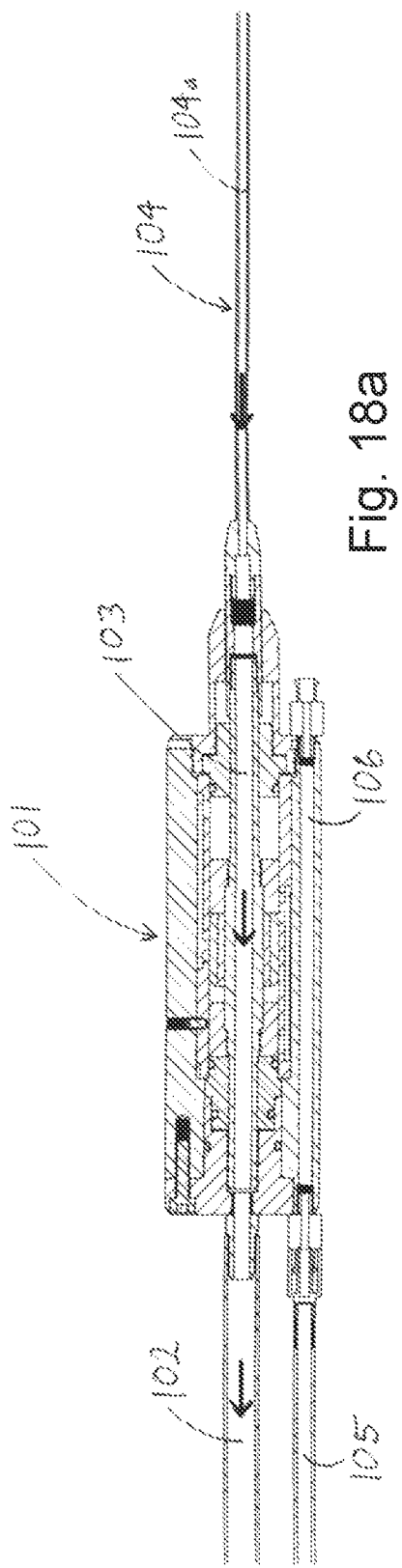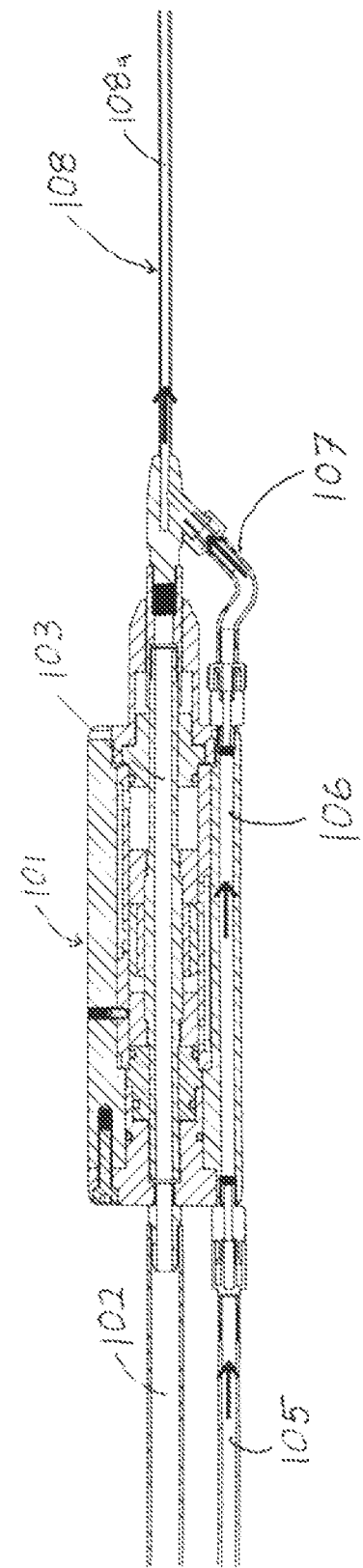

LIPOSUCTION APPARATUS

BACKGROUND

This disclosure relates to an improvement to the Liposuction Apparatus described in U.S. Pat. No. 6,336,925 ("the '925 patent"), patented Jan. 8, 2002. The contents of this prior patent are incorporated by reference herein in their entirety. For the sake of convenience, much of the written description of the '925 patent is contained in the background section below.

Disclosure of the '925 Patent

The '925 patent relates to a liposuction device comprising a suction cannula provided for removing subcutaneous fat through an entry aperture, the cannula having a longitudinal axis and being mounted on a mechanical drive member having an input provided for connecting an energy source and for producing and transmitting a movement to said cannula.

The technique itself of liposuction is known as such. The suction cannula is provided to be introduced under the skin of the patient. The cannula is driven to the zone where the fat must be sucked in. The suction of the fat itself is accompanied with a repeated backward and forward motion and with a depression created inside the cannula.

To assist the user during the liposuction, apparatus with mechanical assistance have been developed provided with a mechanical drive member for producing and transmitting a movement to the cannula. In these devices, such as for example described in U.S. Pat. No. 5,348,535, the produced movement is a translation movement applied to a scrape member. In order to guide the translation movement from this member, these devices comprise an inner cannula sliding within an outer guiding cannula. The outer cannula is thus provided for guiding the translation movement from the inner cannula, whereas the inner cannula serves as suction cannula.

The drawback of the device according to U.S. Pat. No. 5,438,535 is that the translation movement of the inner cannula with respect to the outer cannula provokes a "guillotine" or cutting effect, i.e. it may provoke the cut of the vessels and the nerves. This guillotine effect almost necessarily imposes a general anesthesia of the patient. Furthermore, the fat risks to infiltrate between the inner cannula and the outer cannula, which can provoke a blocking of the translation movement. The known device has also the inconvenience that, due to the presence of a double cannula, i.e. an inner cannula sliding within an outer cannula, the diameter of the cannula is relatively high. If one wishes to reduce the diameter of the outer cannula to allow easier within the body of the patient, the diameter of the inner cannula will also be reduced, which reduces the fat suction flow.

Another liposuction device is described in U.S. Pat. No. 5,352,194. The drive member of this device is provided for producing a translation movement having an amplitude of at least 1 cm. Such an amplitude produces a scrape effect which is dangerous since the user risks exceeding the limits of the region to be liposuctioned and injuring the patient in this way. Furthermore, the larger the amplitude, the larger the reaction will be, which continuously provokes the back motion of the user's wrist and reduces in this way the precision of the accomplished work.

Another liposuction device is described in patent application FR 2,691,624. This device is an ultrasound device, wherein the drive member is provided for producing a vibration movement at ultrasound frequency. Such a device turned out to be not very efficient, since the vibration movement at ultrasound frequency has to dispose the fat cells for subsequent suction. This technique is very slow. In addition, serious burns and cutaneous necrosis can occur.

The object of the '925 patent is to realize a liposuction device the use of which causes considerably less damage on the vessels and nerves, while achieving a mechanical assistance which allows to remove efficiently subcutaneous fat of the patient.

To this object, the liposuction device according to the '925 patent is characterized in that the movement of the cannula is a nutation movement comprising vibration component perpendicular to the axis of the cannula and a translation component according to the axis of the cannula, wherein the translation component has an amplitude less than 1 cm.

The transmission of such nutation movement to the cannula has a double effect. On the one hand, the vibration component allows the cannula to perform a vibration movement when the latter is situated in the subcutaneous fat tissue. This movement will induce a vibration in the fat, allowing to easily introduce the fat in the cannula. On the other hand, the translation component amplifies the vibration component and insures in this way an efficient liposuction. The translation movement allows also to progress very easily and more smoothly the cannula within the skin of the patient. Limiting the amplitude of the translation component to a value less than 1 cm, the fat can easily be sucked in within its expansion limit while limiting considerably the risk to exceed the zone to be treated. The movement transmitted by the drive member creates a sinusoidal wave which extends along the cannula provoking a nutation force which contributes to dislocate the fat and to realize a real emulsion of the fatty tissue.

It has been established during experiments (of the '925 patent) that a little amount of blood was extracted through the cannula, clearly indicating that the liposuction performed with the device according to the '925 patent considerably limits vessels and nerves lesions compared to previous devices with mechanical assistance, wherein there is either a guillotine effect or a scrape effect, or an inefficient liposuction. A local anesthesia is therefore sufficient. Due to the absence of two cannulas sliding within one another, the diameter of the cannula introduced under the skin of the patient can be relatively limited, allowing to access more easily to zones of the human body having a relatively restricted access, such as the chin and the ankle, and limits furthermore the dimensions of scars formed on the skin of the patient.

In a first preferred embodiment of a device according to the '925 patent, said movement produced by the drive member has a frequency between 10 and 500 Hz, preferably less than 250 Hz and most preferably approximately equal to 15 Hz. It has been found that such a frequency range allows to obtain efficient results in combination with the translation movement having an amplitude of less than 1 cm.

In a second preferred embodiment, the device according to the '925 patent comprises a handle wherein said drive member is housed. This facilitates handling of the device according to the '925 patent.

Preferably, the device comprises in addition a control member provided to control starting and stopping the drive member. In particular, the control member is a switch housed in said handle, or is formed by a control pedal cooperating with said drive member. The user can in this way easily control starting and stopping the device, in particular by controlling and holding the device with the same hand or by controlling the device by means of one of his feet.

Preferably said drive member is provided for functioning with compressed air and comprises a pneumatic piston for producing a backward and forward motion. The use of compressed air allows to realize a device which is easy to sterilize.

In another preferred embodiment of the liposuction device according to the '925 patent, the device comprises in addition a cavity for a thumb, said cavity and said aperture being positioned on either side of the cannula axis. This embodiment allows the entry aperture to be directed towards the depth of fatty tissue and not towards the skin of the patient when the operator has introduced the cannula under the skin of a patient and has placed his thumb within the cavity.

Preferred Embodiments of the '925 Patent

FIG. 1 shows an example of an embodiment of a liposuction device according to the '925 patent. In the shown example, the device uses compressed gas, preferably compressed air, in particular sterile dehydrated medical air, as energy source. Due to the medical use, the device with compressed air has the advantage to be easily sterilized. Other sources of energy can however be used such as electric current, magnetic induction or a liquid under pressure. The advantage however to use compressed air compared to electrical current is that it avoids overheating of the device to a considerable extent when the movement is blocked, for example due to a block up of the cannula.

The liposuction device 1 comprises a housing 2 which forms at the same time the handle of the device. Inside the housing, a mechanical drive member is housed to which the sucking cannula 3 is connected, said cannula presenting at least one aperture 14. The cannula 3 has preferably a diameter in the order of 1.5 to 6 mm, in particular approximately 3, 4 or 5 mm, in function of the fat layer to be sucked in. This limited diameter allows an easy access to locations of the human body. The cannula has a smooth surface and is preferably coated with a layer of Teflon®. The apertures 14 are preferably 1 to 3 in number having a diameter of 2 to 5 mm, the apertures being preferably located at the height of the free end of the cannula. The compressed gas is provided by means of a conduct 5 connectable to a source of compressed gas. Cannula 3 is connected through the housing to a discharge conduct 6 which ends in a collector 7 of the sucked fat through the cannula. The collector 7 is also connected through a conduct 8 connected to a unit (not shown in the drawing) provided for creating a depression inside the cannula, as for example a vacuum cleaner.

The housing 2 comprises also a control member, for example a switch 4, which controls starting and stopping of the drive member. According to another embodiment of the '925 patent, a control pedal is provided for starting and stopping the device. Preferably, the control member 4 controls also the suction source which causes the depression inside the cannula. In this way, the user can control with one and same movement the entire functioning of the device according to the '925 patent.

According to a first embodiment of the '925 patent, the drive member located inside the housing, comprises a cylinder 10 and a pneumatic piston 11 driven by the compressed gas provided through conduct 5. The piston 11 acts on the cannula 3 which is connected to the piston 11. A protection cap 13 protects the exit of the cannula at the height of the handle. Preferably, the pressure of the compressed gas is set between 1 and 5 bar as a function of the hardness of the fat to be sucked. For a fat harder or more fibrous, one will tend to use a pressure of 4 to 5 bar, whereas for a more soft and less fibrous fat, one will tend to choose a pressure of less than 4 bar.

Preferably, as illustrated in FIG. 3, the handle presents a cavity 15 provided for placing the user's thumb, said cavity 15 and said aperture 14 being positioned at each side of the axis 16 of the cannula. When the user, having introduced the cannula under the skin 17 of a patient, places his thumb in the cavity, this causes that the entry aperture is directed towards the depth of the fatty tissue and not towards the skin of the patient, ensuring in this way a maintenance of the aperture in the fat to be sucked.

The compressed gas provided to cylinder 10 will provoke a backward and forward movement to piston 11 within the cylinder. Preferably, the movement of the piston is provoked by compressed gas in the two directions. It is also conceivable that the movement of the piston is provoked by compressed gas only in one direction, and that the movement in the other direction is ensured through a spring. The backward and forward motion has a frequency preferably ranging between approximately 10 to 500 Hz, in particular approximately 15 or 200 Hz. The used frequency is chosen according to the material used for the piston. Indeed, the resonance characteristics of the chosen material will influence the vibration wave. The chosen materials are for example ceramic or metal comprising for example stainless steel of aluminum. For stainless steel, a frequency of approximately 15 Hz is for example used.

The backward and forward frequency of the piston causes a vibration wave at the end of the cannula. A nutation movement is created in this way, comprising vibration component perpendicular to the axis of the cannula and a translation component according to the axis of the cannula. The amplitude of the translation component is less than 1 cm for limiting to the maximum extent lesions to vessels and nerves of the patient. In particular, the amplitude is in the order of 3 to 5 mm. It should be noted here that amplitudes of 2 and 6 mm are also comprised.

The amplitude of the vibration component at the end of the cannula is according to the length of the cannula. The longer the cannula, the larger the amplitude of the vibration component at the end of the cannula. The length of the used cannulas is in the order of 5 to 35 cm. When using a cannula having a length of approximately 25 cm and a backward and forward frequency of 15 Hz, one can obtain an amplitude in the order of 1 cm at the free end of the cannula. This signifies that the free end of the cannula describes a nutation movement within a circle, such as illustrated in FIG. 5, wherein the circle has a diameter in the order of 2 cm. The size of the nutation movement can also be expressed as a nutation angle α such as illustrated in FIG. 5. In the case of a cannula of 25 cm and an amplitude of 1 cm, the angle α is in the order of 2.3 degrees. The amplitude can also have an amplitude less than 1 cm, for example in the order of 3 to 5 mm.

For allowing the nutation movement, a free space 18 is provided between the cannula and the handle, such as illustrated in FIG. 4 showing a section of a portion of the device according to FIG. 3.

In this way, the cannula 3 will receive the translation movement which is imposed not only when introducing the cannula under the skin of the patient, but also during the liposuction itself. Upon use, the vibration of the cannula is directly transmitted to the fat which is dissociated, dislocated or split and beats it so to speak in a foam which enables it to enter easily in apertures 14 of the cannula, thereby causing virtually no lesions of the vessels and the nerves of the patient. The translation allows to have the cannula penetrated easily under the skin, since the penetration movement, applied by the user, is assisted with the backward and forward motion of the cannula. By limiting considerably the lesion, the device can even be used under local anesthesia, which is not the case with the known devices with mechanical assistance.

The user does not have necessarily to apply an intense massage nor pinching of the part to be treated, as with devices without mechanical assistance, since it is the vibration motion of the cannula which is transmitted to the fat and which provokes its dislocation and therefore its withdrawal to the entry aperture of the cannula. In practice, it is sufficient for the user to stretch the skin or to press the zone to be treated in order to compress the fat.

Since the user does not have necessarily to apply an intensive massage nor a pinching, the user can concentrate on the guiding of the cannula at the locations where the fat has to be dislocated and removed. This allows thus the user to guide decently and with more precision the cannula under the skin of the patient. The hand of the user which holds the handle can work free in any direction of the space and impose the directions in this way to the cannula. In addition, the movement of the cannula, since it is mechanically assisted, is more precise and more regular.

In comparison to previous mechanical assisted devices, the device according to the '925 patent presents the advantage that it does not produce the guillotine effect, painful for the patient and provoked by the translation movement of the inner cannula with respect to the outer cannula. FIGS. 6 to 8 illustrate a longitudinal section view of a second embodiment of the drive member according to the '925 patent. This member 20 is also housed in housing 21 and comprises a piston 22 and also an admission and exhaust circuit illustrated more in detail in FIG. 9. The member comprises a gas admission circuit, preferably compressed air, at the front 26 and at the back 24, each having a front injector (24 a. 26 a) and a rear injector (24 b, 26 b) allowing to inject the gas in the circuit. The gas is supplied through an admission conduct 27 in connection with the injectors. The exhaust of the gas is ensured by an exhaust circuit having a front 25 and a rear 31 part. In FIGS. 6 to 8, the exhaust circuits are illustrated in the plane of the drawing whereas in reality they form an angle of 90 degrees with the admission circuits. This has been done for rendering the description easier understandable and to better explain the functioning. FIG. 9a illustrates a cross-section view whereas FIGS. 9b to 9e illustrate each time longitudinal sections at the height of which the admission and exhaust circuits are situated. A selector 23 is housed in a cavity of the outer wall of piston 22. The movement of piston 22 inside the drive member is guided by means of bearings 28 and 29. The exhaust circuits 25 and 31 are connected to a pipe 30 allowing the release of the exhaust gas.

When the compressed gas is supplied to the admission conduct and the piston 22 is in initial backward position, such as illustrated in FIG. 6, the gas will penetrate through the front injector 24 a in the rear admission circuit 24. Since the front injector 24a is located near the selector 23, the introduced gas will exert a pressure on the selector 23 causing in this way motion of the latter to the left or to the back of the member. The movement to the back of the selector 23 will further open the admission circuit 24 as illustrated in FIG. 7 where the selector is located in rear position.

The admission circuit 24 can now quickly be filled with compressed gas which will consequently flow to the back of the admission circuit 24. The movement of the selector has also opened the rear injector 24 b causing in this way also an admission of compressed gas at the back of piston 22. The force exerted by the gas at the back of the piston will now cause its movement to the right or the front of the drive member. The movement of the piston causes in its turn that the gas present at the front of the piston will be pushed in the exhaust circuit 31.

When the piston 22 has traveled a sufficient path, it closes the admission to the exhaust circuit 31 as illustrated in FIG. 8. The gas remaining then in the space between the bearing 29 and the piston 22 will be compressed through the movement of the piston and dumps in this way the path of the piston. A pneumatic dumping device is obtained in this way which avoids that the piston strikes the bearing 29.

The movement to the front of the piston 22 will also compress the gas present in the front admission circuit 26, through the intermediary of the front injector 26 b. The gas will circulate in this way in the front admission circuit 26 to reach the rear circuit. When arrived to this balance position, the unit is now in a configuration which will allow to leave in the opposed direction.

Since the compressed gas continues to arrive in the admission canal 27 and the injector 26a is free, the gas can enter the front admission circuit 26 and exert a pressure on the selector 23 pushing it to the front. The movement to the front of the selector will further open the front admission circuit 26 and the injector 26a, allowing the gas to travel in direction of the injector 26b and to fill the front admission circuit. The gas now present at the front of the piston 22 will exert a pressure on the latter and will push it to the back. This movement of the piston will cause in its turn that the gas present in the space between the bearing 29 and the piston will be pushed back in the circuit 24 and in the exhaust circuit 25 from which it reaches the piping 30.

When the piston 22 has traveled a sufficient path, it will close the exhaust circuit 25 and compress the gas in the space between the bearing 29 and the piston. In this way, the movement to the back of the piston is damped and the gas in said space functions as a damping device which avoids that the piston strikes the bearing 29. The gas in the rear admission circuit 24 is compressed and the initial position (FIG. 6) is found again, allowing to start again the movement.

The judicious position of the exhaust injectors has as effect to produce a damping at the end of the path, which limits the movement of the piston and avoids to strike the bearings. This function is also used as overpressure and allows to increase the compression of the gas in the admission circuit opposed to the exhaust circuit (31 to 24; 25 to 26). This reduces the filling time of the admission circuit for the next phase and allows to obtain in this way a higher working frequency and to save the gas consumption.

The movement of the piston is thus preceded by a movement of the selector which functions in phase opposition with respect to the movement direction of the piston.

The back and forth motion exerted by the piston 22 and the manner in which the compressed gas is fed to the piston will cause nutation movement of the cannula. The feeding with small quantities of compressed gas causing the back and forth motion of the piston drives also a bending movement on the axis of the piston. These two movements result then in a nutation movement. The piston tends also to exert a rotation movement which is however prevented due to the presence of a nose 32 at downstream side at the front of the piston.

According to an alternative embodiment of the '925 patent, the drive member is provided to produce only a vibration movement instead of a combination of a vibration and translation movement.

According to the embodiment of the '925 patent illustrated in FIG. 1, the fat, collected in the cannula, is collected laterally through the piping 6 and the container 7. According to an alternative embodiment of the '925 patent, fat is collected, through the axis of the piston 11, which is in this case hollow. This considerably facilitate the evacuation of the fat, since it occurs in the extension of the cannula.

Changes in Practice Since the '925 Patent

Since the issue of the '925 patent, a few notable modifications have been made to the liposuction apparatus described therein. For instance, while the '925 patent does not explicitly show an infiltration fluid cannula, such cannulas have been used to deliver infiltration fluid to a patient in combination with the liposuction apparatus of the '925 patent. An infiltration fluid cannula is attached to the liposuction apparatus of the '925 patent, and infiltration fluid is supplied directly to the infiltration fluid cannula by one end of an infiltration tubing that is connected, at its other end, directly to a source of infiltration fluid. That is, the infiltration fluid cannula is attached to the liposuction apparatus, but infiltration fluid is actually supplied through the separate infiltration tubing which connects directly to the infiltration fluid cannula. Because this separate infiltration tubing extends from the infiltration cannula, it makes handling the liposuction apparatus difficult and unwieldy.

One further development since the issue of the '925 patent is the inclusion of a "nose cone," which is affixed to a front end of the liposuction apparatus of the '925 patent. The nose cone is affixed on the same end of the apparatus as the cannulas, and holds within it a "plastic insert." This plastic insert is analogous to the "nose 32," mentioned in the '925 patent's description above. That is, the plastic insert prevents the cannula from rotating due to the motion of the "piston 22." The '925 patent implies that such rotation of the cannula is undesirable.

This nose cone must first be removed before for cleaning of the apparatus or removal of the plastic insert. In practice the nose cone and plastic insert have several noticeable disadvantages. First, the nose cone has a tendency to get stuck, and the liposuction apparatus must then be sent into a specialty shop in order to remove the nose cone and perform maintenance. Second, the nose cone plastic insert is subjected to significant stresses during liposuction and has a tendency to break, which again requires additional maintenance. Thirdly, as a result of these same stresses, the nose cone plastic insert tends to shed plastic pieces which fall onto (and potentially into) the patient, which is clearly undesirable.

SUMMARY OF THE INVENTION

The present disclosure relates to an improved liposuction apparatus based partially on the liposuction apparatus disclosed in the '925 patent. Except as noted below, and to the extent that they are not mutually incompatible, the embodiments of this disclosure may incorporate any of the various arrangements and embodiments of the '925 patent, alone or in combination.

As mentioned above, there are several problems with the liposuction apparatus of the '925 patent. In order to remedy these problems, an improved liposuction apparatus is proposed. The improved liposuction apparatus may have a handpiece having a front end and a back end opposite to the front end. The device may include a handpiece suction pathway extending through the handpiece from the front end to the back end of the handpiece and a handpiece infiltration fluid pathway extending through the handpiece from the front end to the back end of the handpiece. The handpiece suction pathway and the handpiece infiltration fluid pathway may be separate and distinct. The handpiece may be configured such that when a suction cannula having a suction cannula pathway is attached to the front end of the handpiece, the suction cannula pathway and the handpiece suction pathway are in fluid communication with one another. The handpiece may also be configured such that, when an infiltration fluid cannula having an infiltration cannula pathway is attached to the front end of the handpiece, the infiltration cannula pathway and the handpiece infiltration fluid pathway are in fluid communication with one another.

The handpiece may be configured such that, when an infiltration fluid source pathway is attached to the back end of the handpiece, the infiltration fluid source pathway is in fluid communication with the handpiece infiltration fluid pathway.

The improved liposuction apparatus may include a separate external infiltration fluid tube, which is separate from the infiltration cannula and the handpiece, and fluidly connects the infiltration cannula pathway to the handpiece infiltration fluid pathway. In other embodiments, the external infiltration fluid tube may be an integral part of the handpiece. In yet other embodiments, the external infiltration fluid tube may be an integral part of the infiltration cannula.

The handpiece infiltration fluid pathway may contain infiltration fluid therein. The infiltration fluid may be tumescent fluid.

In some embodiments, the suction cannula and the infiltration fluid cannula may be allowed to rotate based on forces transmitted from one or more pistons, as discussed above. That is, the handpiece may include a motor, like the one described in the '925 patent, for moving the suction cannula and/or the infiltration fluid cannula along a longitudinal axis of the handpiece, and the suction cannula and the infiltration fluid cannula are not prevented from rotating/spinning due to movements of the motor. Likewise, the piston-based actuator may allow for the nutational movement described in the '925 patent without restricting rotation or spinning of the suction cannula/infiltration fluid cannula.

BRIEF DESCRIPTION OF THE DRAWINGS

The invention will now be described more in detail by means of the Drawings illustrating an example of the device according to the invention. In the Drawings:

FIG. 1 illustrates an overall assembly of a liposuction device according to the '925 patent.

FIG. 3 illustrates a portion of a preferred embodiment of the device according to the '925 patent.

FIG. 10 is a prior art configuration of an infiltration cannula.

FIGS. 12a and 12b show an oblique view of the embodiment of FIGS. 11a and 11b.

FIGS. 13a and 13b show an assembled side view of the embodiment of FIGS. 11a and 11b.

FIGS. 14a and 14b show an assembled oblique view of the embodiment of FIGS. 11a and 11b.

FIGS. 15a and 15b show an enlarged view of the front end of the handpiece and the suction cannula of the embodiment of FIGS. 11a and 11b.

FIGS. 16a and 16b show an enlarged view of the front end of the handpiece and the infiltration cannula of the embodiment of FIGS. 11a and 11b.

FIGS. 17a and 17b show a plan view of the arrangements in FIGS. 15a and 16a, respectively.

FIGS. 18a and 18b show a zoomed-out plan view of the embodiment of FIGS. 11a and 11b.

In these Drawings, the same reference numerals are used to denote the same and/or similar elements.

DETAILED DESCRIPTION OF THE INVENTION

As shown in FIG. 10c a typical infiltration cannula 208, is connected directly to one end of an infiltration fluid source tubing 205. The other end of the infiltration source tubing 205 is connected directly to the infiltration fluid supply. As mentioned above, the connecting of the source tubing 205 directly to the infiltration cannula 208 makes handling any liposuction apparatus to which the infiltration cannula 208 is connected awkward and unwieldy.

Figure 11A:
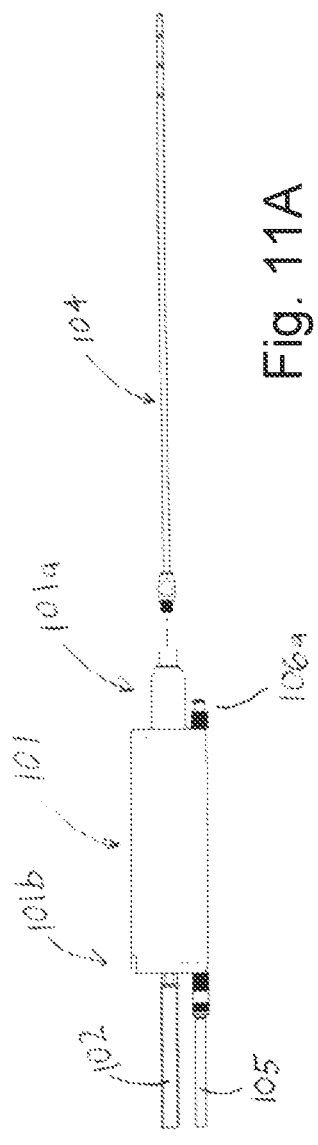
FIGS. 11a and 11b illustrate an assembly side view of a preferred embodiment of the improved liposuction apparatus of the current disclosure.
Figure 11B:
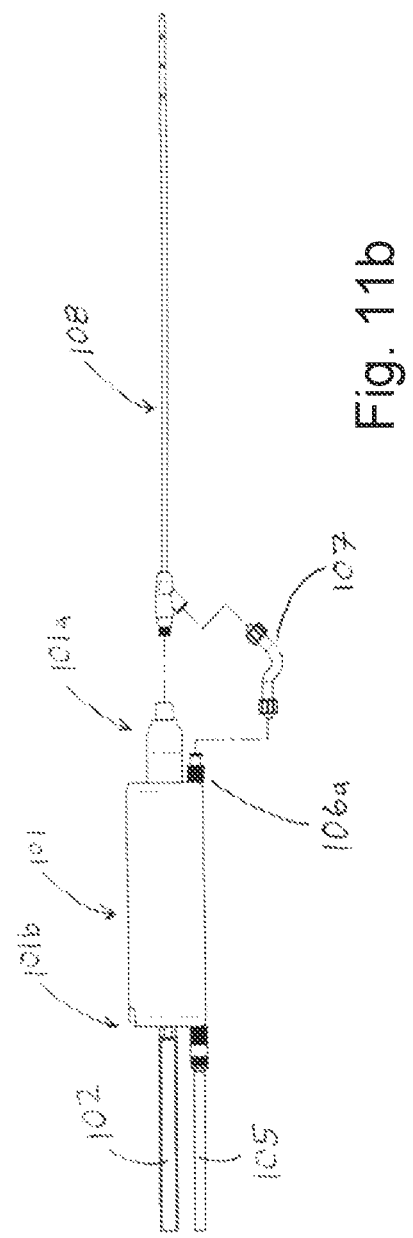

FIGS. 11a and 11b show a side view of a preferred embodiment of the improved liposuction apparatus. As seen in those figures, the apparatus includes a handpiece 101, having a front end 101a, and a back end 101b. The front end 101a is configured to connect to a suction cannula 104 and/or an infiltration fluid cannula 108. The back end 101b of the handpiece 101 is configured to connect to a suction supply pathway 102 that supplies suction. The back end 101b of the handpiece 101 is also configured to connect to an infiltration fluid source pathway 105 that supplies infiltration fluid to the handpiece 101. An external infiltration fluid tube 107 may be provided to connect an infiltration cannula pathway 108a of the infiltration cannula 108 to a front-end infiltration fluid port 106a of the handpiece 101. FIGS. 12a-17b show various views of this same embodiment.

FIGS. 18a and 18b give a more detailed view of the inside of the handpiece 101 according to the preferred embodiment. As shown in those figures, the handpiece 101 contains a handpiece suction pathway 103, extending through the handpiece 101 from the front end 101a of the handpiece 101 to the back end 101b of the handpiece 101. The handpiece also contains a handpiece infiltration fluid pathway 106, extending through the handpiece 101 from the front end 101a of the handpiece 101 to the back end 101b of the handpiece 101. As shown in the figures, the handpiece suction pathway 103 and the handpiece infiltration fluid pathway 106 may be substantially parallel to one another.

As FIG. 18a shows, when the suction cannula 104 is attached to the front end 101a of the handpiece 101, the handpiece suction pathway 103 is in fluid communication with a suction cannula pathway 104a of the suction cannula 104. In this configuration, the handpiece infiltration fluid pathway 106 is not in fluid communication with the suction cannula pathway 104a.

Conversely, as shown in FIG. 19b, when the infiltration fluid cannula 108 is attached to the front end 101a of the handpiece 101, the handpiece infiltration fluid pathway 106 is in fluid communication with an infiltration cannula pathway 108a of the infiltration cannula. In this configuration, the handpiece suction pathway 103 is not in fluid communication with the infiltration cannula pathway 108a. And, in both the configuration of FIG. 18a and the configuration of FIG. 18b, the suction supply pathway 102 is in fluid communication with the handpiece suction pathway 103, and the infiltration fluid source pathway 105 is in fluid communication with the handpiece infiltration fluid pathway 106.

Thus, as shown in FIGS. 11a-18b, the supply of infiltration fluid is provided in the back end 101b of the handpiece 101, not directly to the cannula itself, as show in prior art FIG. 10. Routing the infiltration fluid through the handpiece infiltration fluid pathway 106 thus remedies the awkwardness and unwieldiness of using the prior art liposuction apparatus.

As discussed above, in some embodiments, the improved liposuction apparatus may include a separate external infiltration fluid tube 107, which is separate from the infiltration cannula 108 and the handpiece 101, and fluidly connects the infiltration cannula pathway 108a to the handpiece infiltration fluid pathway 106. However, in other embodiments, the external infiltration fluid tube 107 (and consequently the front-end infiltration fluid port 106a) may be an integral part of the handpiece 101. Alternatively, the external infiltration fluid tube 107 may be an integral part of the infiltration cannula 108.

Figure 2:
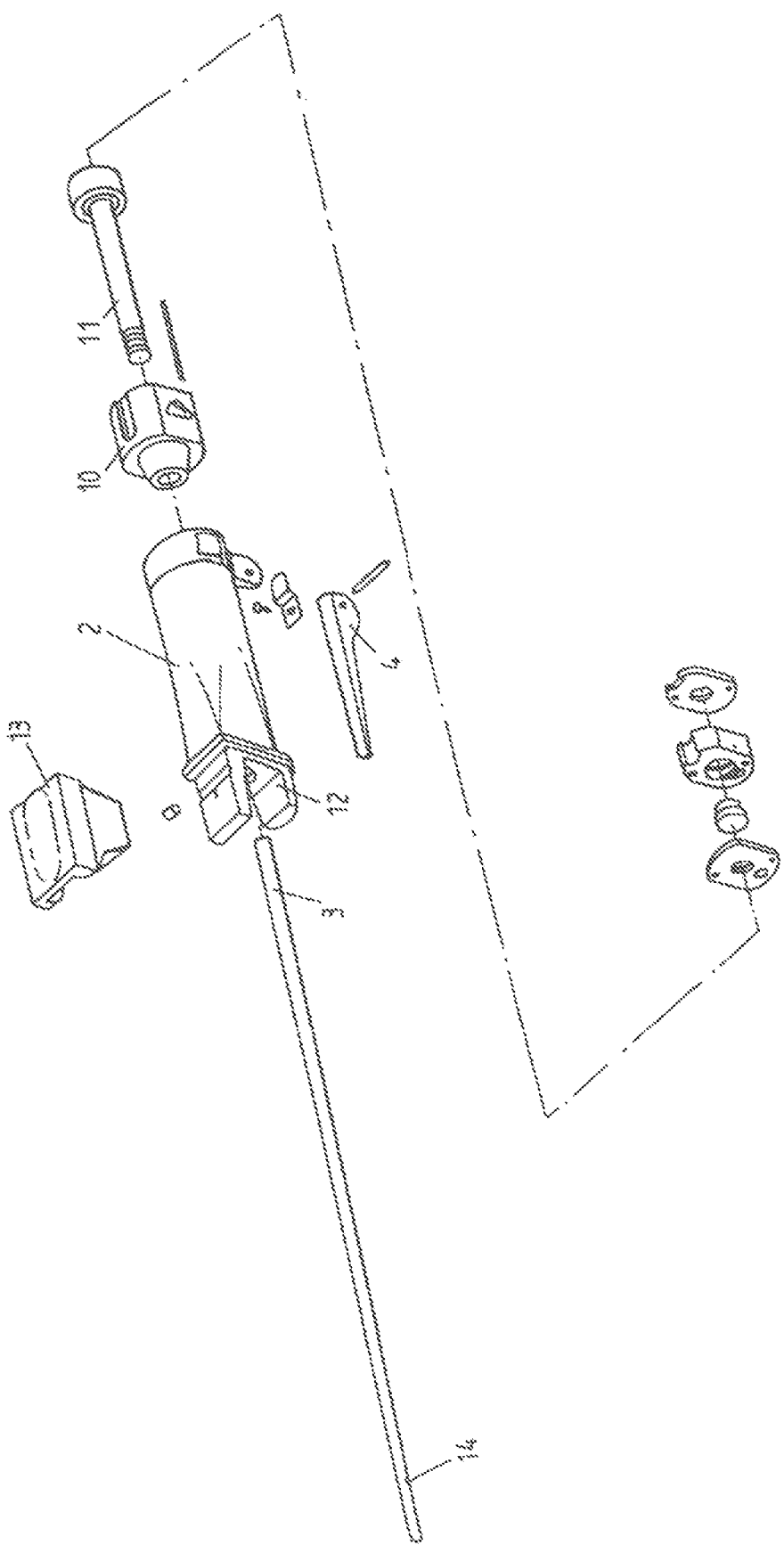
FIG. 2 illustrates the principal components of a device according to the '925 patent.
Figure 4:
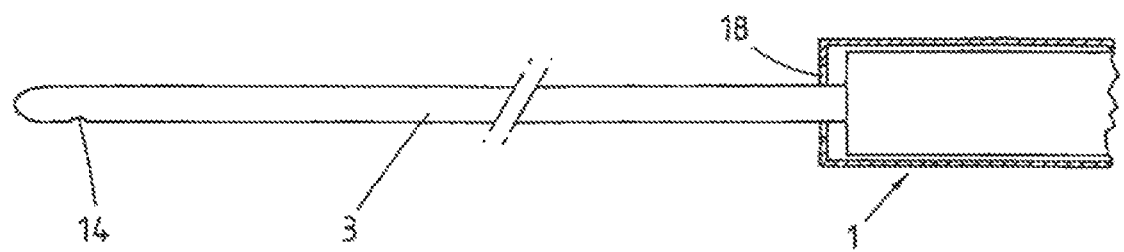
FIG. 4 is a section view of a portion of FIG. 3.
Figure 5:
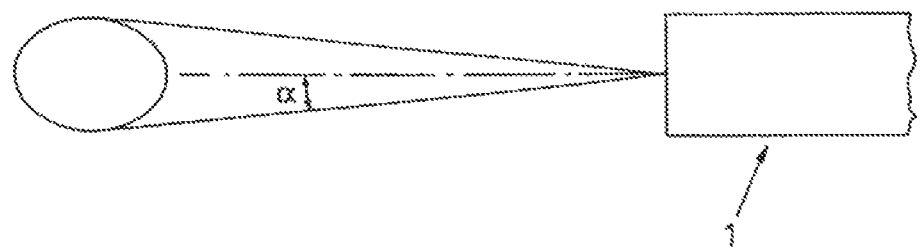
FIG. 5 schematically illustrates the nutation movement transmitted to the cannula in the '925 patent.
Figure 6:
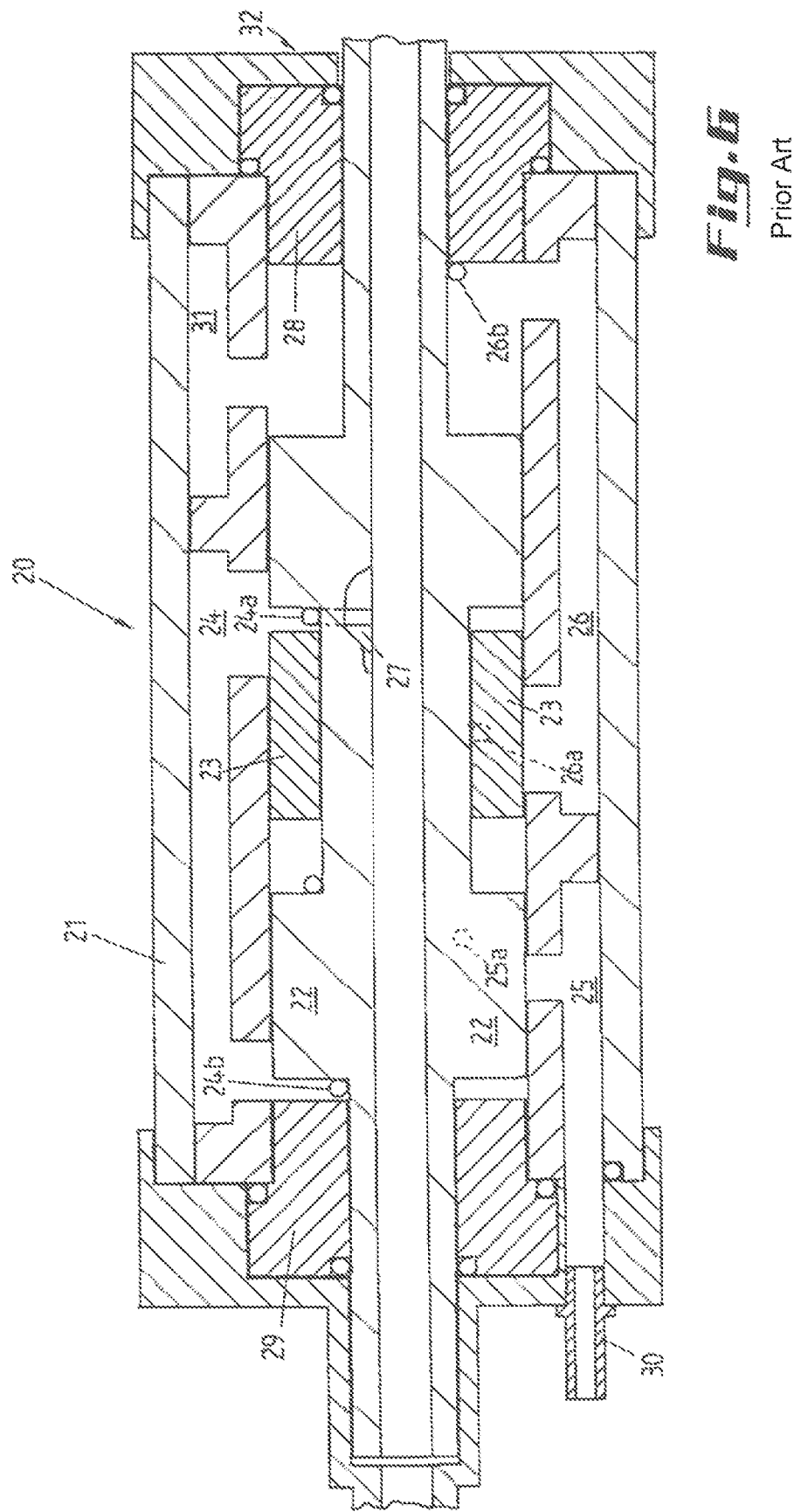
FIGS. 6 to 8 illustrate a section view of different working phases of a motor allowing to produce the movement to be imposed to the cannula in the '925 patent.
Figure 7:
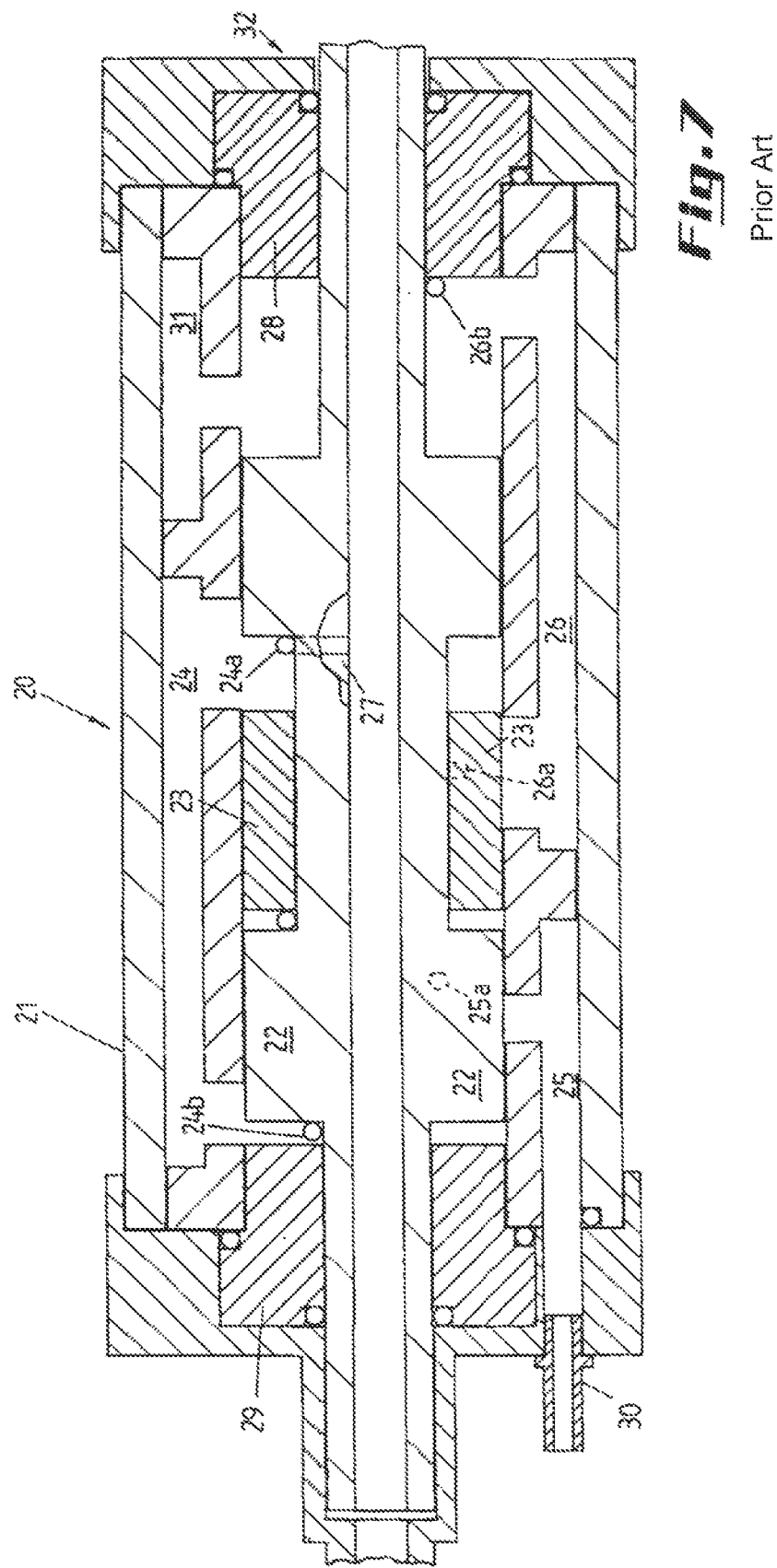
Figure 8:
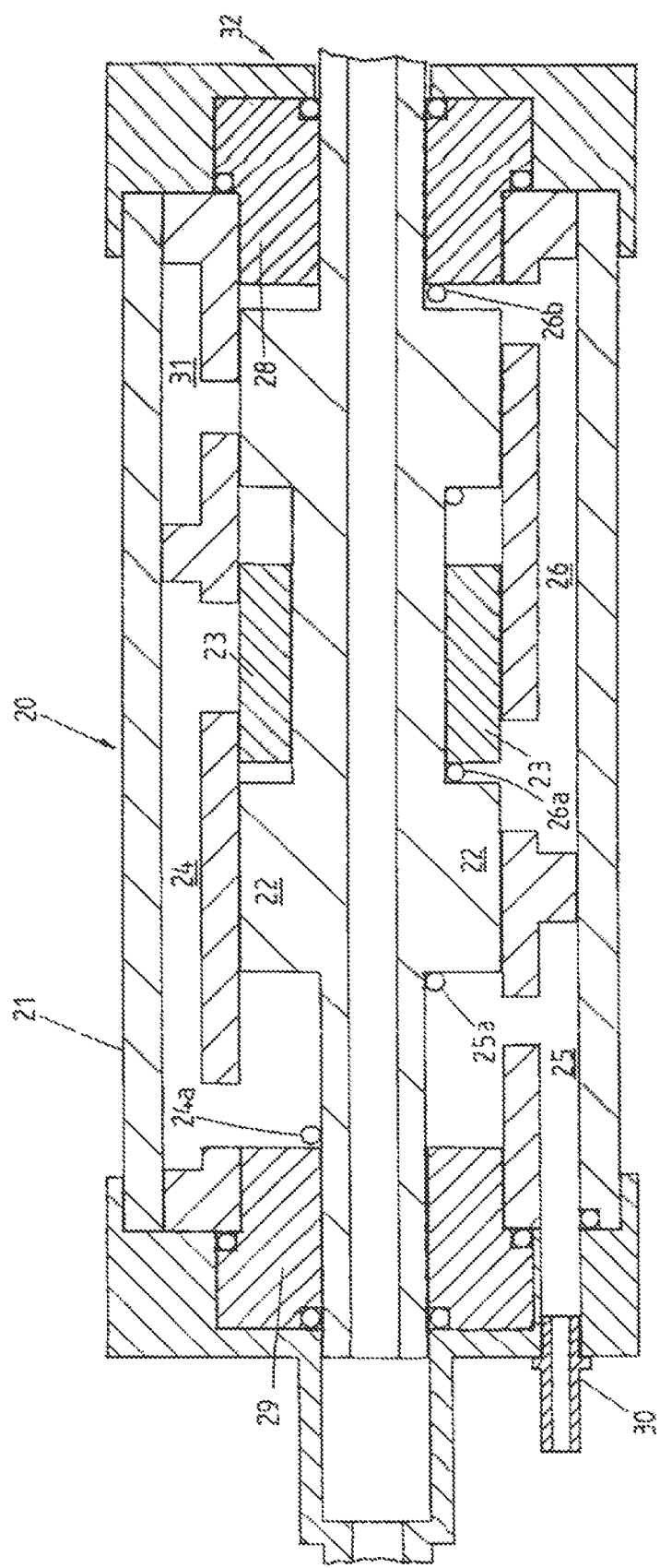
Figure 9A:
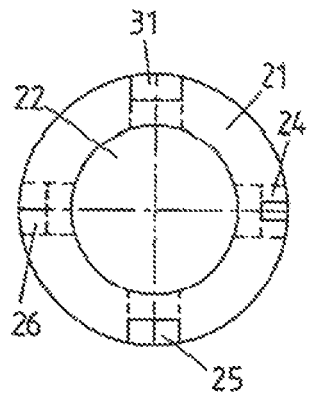
FIGS. 9*a* to 9*e* illustrate the configuration of admission and exhaust circuitry of the motor in the '925 patent.
Figure 9B:
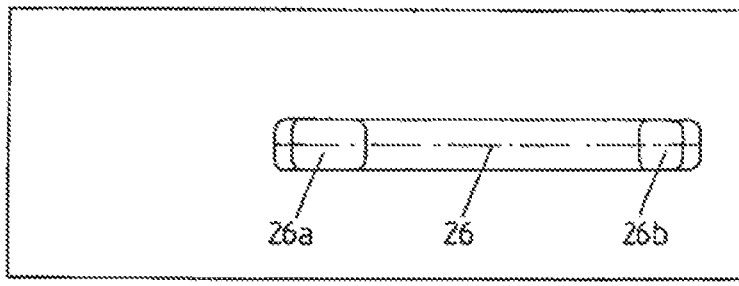
Figure 9C:
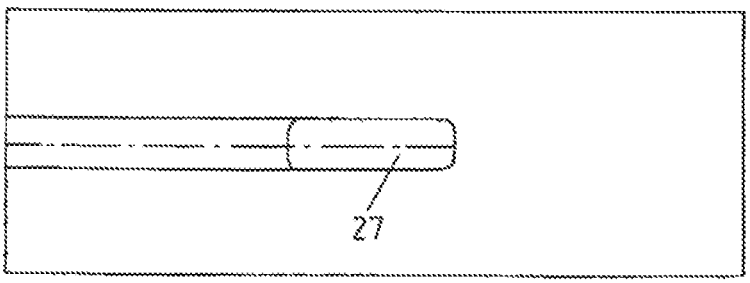
Figure 9D:
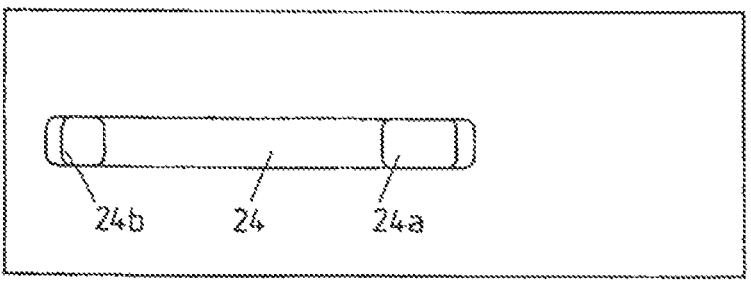
Figure 9E:
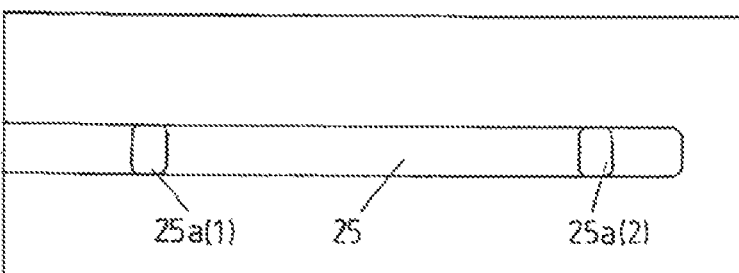

As mentioned above, in some embodiments of the improved liposuction apparatus, the "nose cone" with the "plastic insert" (analog to the "nose 32" in the '925 patent) are specifically not included. As discussed in the '925 patent, the purpose of the "nose 32" (shown in FIGS. 6-8) is to prevent "rotational" movement of the cannula 3 (shown in FIGS. 1-4) when it is inserted into the patient. While the '925 patent takes as a given the importance of eliminating this rotational movement, practical use has shown that rotational movement of a cannula is not as undesirable as the increased maintenance frequency, increased maintenance cost, and the increased risk of shedding plastic pieces into/onto the patient that arise from the "nose cone" and "plastic insert" combination. Thus, in some embodiments of the improved liposuction apparatus, the plastic insert is removed, reintroducing some rotational motion of the cannula, but significantly reducing both maintenance problems and risk to the patient.

As mentioned above, the improved liposuction apparatus described here may or may not include any of the compatible components described in the '925 patent, alone or in combination. For instance, the improved liposuction apparatus may be used with or without the "back and forth motion" and "nutational motion" generated by the configurations described in the '925 patent.

What is claimed is:

1. A liposuction apparatus comprising: a handpiece having (i) a front end and (ii) a back end opposite to the front end, whereby the handpiece extends along a first longitudinal axis from the front end to the back end; a handpiece suction pathway extending through the handpiece from the front end to the back end of the handpiece along the first longitudinal axis; and a handpiece infiltration fluid pathway extending through the handpiece from the front end to the back end of the handpiece along a second longitudinal axis parallel to the first longitudinal axis wherein: the handpiece suction pathway and the handpiece infiltration fluid pathway being separate and distinct, and the handpiece is configured such that: when a suction cannula having a suction cannula pathway is attached to the front end of the handpiece, the suction cannula pathway and the handpiece suction pathway are in fluid communication with one another, and when an infiltration fluid cannula having an infiltration fluid cannula pathway is attached to the front end of the handpiece instead of a suction cannula, the infiltration fluid cannula extends along the first longitudinal axis, and when an infiltration fluid cannula having an infiltration fluid cannula pathway is attached to the front end of the handpiece, the infiltration fluid cannula pathway and the handpiece infiltration fluid pathway are in fluid communication with one another; wherein a portion of the infiltration fluid cannula is seated within the handpiece suction pathway and blocks the handpiece suction pathway; and an external infiltration fluid tube located fluidly between the infiltration cannula pathway and the handpiece infiltration fluid pathway such that the external infiltration fluid tube allows for fluid communication between the infiltration cannula pathway and the handpiece infiltration fluid pathway, wherein the external infiltration fluid tube is bent and separate and distinct (i) from the infiltration fluid cannula and (ii) from the handpiece.

2. The liposuction apparatus in claim 1, wherein the handpiece is configured such that, when an infiltration fluid source pathway is attached to the back end of the handpiece, the infiltration fluid source pathway is in fluid communication with the handpiece infiltration fluid pathway.

3. The liposuction apparatus in claim 1, wherein the external infiltration fluid tube is an integral part of the handpiece.

4. The liposuction apparatus in claim 1, wherein the external infiltration fluid tube is an integral part of the infiltration fluid cannula.

5. The liposuction apparatus in claim 1, wherein the handpiece infiltration fluid pathway contains infiltration fluid therein.

6. The liposuction apparatus in claim 5, wherein the infiltration fluid is tumescent fluid.

7. The liposuction apparatus in claim 1, wherein the handpiece includes a motor configured to move the suction cannula and/or the infiltration fluid cannula along a longitudinal axis of the handpiece, and the suction cannula and the infiltration fluid cannula are not prevented from spinning due to movements of the motor.

8. A method of using the liposuction apparatus of claim 1, the method comprising:
   providing infiltration fluid to a liposuction patient, the infiltration fluid passing through the handpiece infiltration fluid pathway before being supplied to the patient.

9. The method of claim 8, wherein the infiltration fluid is tumescent fluid.

\* \* \* \* \*